United States Patent [19]
Maruyama et al.

[11] Patent Number: 5,431,919
[45] Date of Patent: Jul. 11, 1995

[54] RUMINAL DRUG DELIVERY DEVICE

[75] Inventors: Fred Maruyama, San Jose; John P. Carr, Sunnyvale; James B. Eckenhoff, Los Altos, all of Calif.

[73] Assignee: ALZA, Palo Alto, Calif.

[21] Appl. No.: 81,743

[22] Filed: Jun. 23, 1993

[51] Int. Cl.⁶ .................................................. A61K 9/24
[52] U.S. Cl. ..................................... 424/473; 424/438; 604/892.1
[58] Field of Search .............................. 424/473, 438

[56] References Cited

U.S. PATENT DOCUMENTS

| | | | |
|---|---|---|---|
| 4,595,583 | 6/1986 | Eckenhoff et al. | 424/15 |
| 4,612,186 | 9/1986 | Eckenhoff et al. | 424/15 |
| 4,772,474 | 9/1988 | Eckenhoff et al. | 424/465 |
| 4,844,984 | 7/1989 | Eckenhoff et al. | 424/438 |
| 4,872,873 | 10/1989 | Zingerman | 604/892.1 |
| 5,045,082 | 9/1991 | Ayer et al. | 604/892.1 |
| 5,122,128 | 6/1992 | Cardinal et al. | 604/890.1 |
| 5,206,024 | 4/1993 | Peery et al. | 424/438 |
| 5,213,809 | 5/1993 | Wright e tal. | 424/473 |

FOREIGN PATENT DOCUMENTS 9011856 10/1990 WIPO .

Primary Examiner—D. Gabrielle Phelan
Attorney, Agent, or Firm—Richard T. Ito; Edward L. Mandell; Steven F. Stone

[57] ABSTRACT

The present invention is concerned with improving the delivery of a drug from a ruminal delivery device to give a consistent delivery of drug to the ruminal environment. Thus, the invention is directed to an improved ruminal drug delivery device comprising a semipermeable membrane having an exit orifice and defining a compartment, the compartment containing a swellable osmotic agent expandable member, a drug to be dispensed, a density element and, optionally, a partition layer between the osmotic expandable member and the drug formulation, wherein the improvement comprises an essentially gas-impermeable barrier means that separates the density element from the other components within the delivery device for isolating gases evolved from the density element from the other components within the delivery device. The invention is also directed to methods and articles for providing a consistent delivery of drug from a ruminal drug delivery device.

24 Claims, 4 Drawing Sheets

RUMINAL DRUG DELIVERY DEVICE

FIELD OF THE INVENTION

This invention relates to ruminal drug delivery devices. More particularly, this invention relates to a ruminal device having improved delivery activity.

BACKGROUND OF THE INVENTION

Ruminant animals, including cattle, sheep, giraffe, deer, goats, bison and camels, and more particularly cattle and sheep, comprise an important group of animals that require periodic administration of medicines, nutrients and other biologically active agents (which are hereinafter referred to in their broadest sense as "drugs") for the treatment and alleviation of various conditions and for better health.

Ruminants have a complex three or four compartment stomach, with the rumen being the largest compartment. The rumen serves as an important location for receiving and absorbing medicines and nutrients into other compartments including the abomasum and the intestine.

There are numerous ruminal delivery devices known in the art which are capable of prolongedly releasing drugs. These devices are easily swallowed by the ruminant or otherwise introduced into the rumen and remain within the rumen for a long period of time without being regurgitated or otherwise expelled. Typical devices having an osmotic portion which imbibes ruminal fluid and expands, forcing a liquid or paste drug portion of the device through an orifice into the rumen, are those disclosed in U.S. Pat. Nos. 4,595,583 and 4,612,186, the disclosures of which are incorporated herein by reference.

In order to insure that these devices remain in the rumen for a prolonged period of time, a density element is often incorporated into the device. Typically, the density element is manufactured from a material such as iron or steel, iron shot, iron shot coated with iron oxide, magnesium alloy, copper oxide or mixtures of cobalt oxide and iron powder, and the like. Such density elements typically have sufficient density to bring the overall density of the delivery device to a level greater than the density of ruminal fluid (approximately 1 gm/mL) and preferably to an overall density of at least 2 gm/mL.

The osmotic ruminal delivery device or bolus has encountered some difficulties, however; the daily output of the bolus has been seen to often be highly erratic. It has been found that density elements made from materials such as iron, magnesium or zinc are susceptible to corrosion in water or ruminal fluids. This corrosion causes production of gases, which gases enter into other portions of the device and accumulate as gas bubbles which can cause fissures within the drug formulation and/or the osmotic expandable member. The presence of such fissures can cause gaps in the flow of drug formulation or a rapid expulsion of a portion of the lo formulation. Typically, the formation of a fissure causes a rapid expulsion of a portion of the formulation (fissure/bubble formation) followed by gaps or a decrease in the flow of drug formulation (fissure closure or expulsion through orifice). Thus, erratic flow is observed with days of low output and days of high output. In one effort to decrease corrosion, density elements of sintered metal have been impregnated during manufacture with an inert hydrophobic material such as silicone oil, mineral oil or wax (see, U.S. Pat. No. 5,206,024 and PCT patent publn. WO 90/11856). This method, while apparently successful, has the disadvantages of being a time-consuming process during, and adding considerable expense to, the manufacture of the ruminal delivery device. Additionally, this is not a practical solution when the density element is not of the fragmentable sintered type disclosed in the above publications.

SUMMARY OF THE INVENTION

The present invention is concerned with improving the delivery of a drug from a ruminal delivery device to give a consistent delivery of drug to the ruminal environment. Thus, the invention is directed to an improved ruminal drug delivery device comprising a semipermeable membrane defining a compartment, the compartment containing an osmotic expandable member, a drug to be dispensed, a density element, an exit orifice and, optionally, a moveable partition layer between the osmotic expandable member and the drug formulation, wherein the improvement comprises an essentially gas-impermeable barrier means that separates the density element from the other components within the delivery device for isolating gases evolved from the density element from the other components within the delivery device.

This invention is also directed to an article which improves the performance of a ruminal drug delivery device. The article comprises an essentially gas-impermeable insert which is sized and shaped to be placed between the density element and the other components within the ruminal device. The insert acts as a barrier means to protect the drug formulation and other components from gas evolved during corrosion of the density element, thus providing a more constant and consistent delivery profile of drug from the device.

The invention is further directed to a method for providing a consistent delivery of drug from a ruminal delivery device, the method comprising placing into the rumen of a ruminant animal an improved ruminal delivery device of the present invention, and allowing fluid from the ruminal environment to be taken up by the osmotic expandable member for delivering the drug from the device at a consistent rate.

DETAILED DESCRIPTION OF THE INVENTION

It has been found that placing a barrier between the density element and the other components of a ruminal delivery device as generally disclosed herein substantially reduces erratic delivery of drug from the device, while at the same time being simple and inexpensive to incorporate into the manufacture of the device.

The improved controlled release ruminal delivery device of this invention comprises a semipermeable membrane which defines a compartment, the compartment being divided into first and second portions by an interface or, in certain embodiments, by a moveable partition. The first compartment portion contains a swellable osmotic material and the second compartment portion contains a drug or medicament or other therapeutic agent to be dispensed, generally in a semiliquid, gel or paste form. A density element resides within the compartment and may be positioned either adjacent to the exit orifice or at the end opposite from the exit orifice or elsewhere in the device. An orifice having an inside cross-sectional shape and extending through the membrane and, when the density element is adjacent to the orifice, through the density element connects the second compartment portion with the exterior of the device. When the device is in contact with water such as is found in the ruminal fluid of a ruminant, the semipermeable membrane allows water to pass therethrough which is imbibed by the swellable osmotic material which forces the interface between the osmotic material and the medicament to move the medicament to be dispensed through the orifice. The improvement of this invention comprises a barrier means which is placed between the density element and the other components within the device to separate the density element from the other components. The barrier means is essentially impermeable to gases that are evolved as a result of corrosion of materials making up the density element and acts to keep the evolved gases from passing into the other components, and especially the drug formulation, within the device.

This invention will be described with respect to ruminal delivery devices of the type shown in the Figures, but it is not limited to the specific devices disclosed. The ruminal delivery device designs illustrated herein are merely exemplary of devices known to the art, and the gas barrier means of this invention can be adapted to fit in a ruminal delivery device and with a density element of any configuration. In the following description of the Figures, the Figures are not necessarily drawn to scale and like elements in the different Figures will be referred to by the same number.

Figure 1:
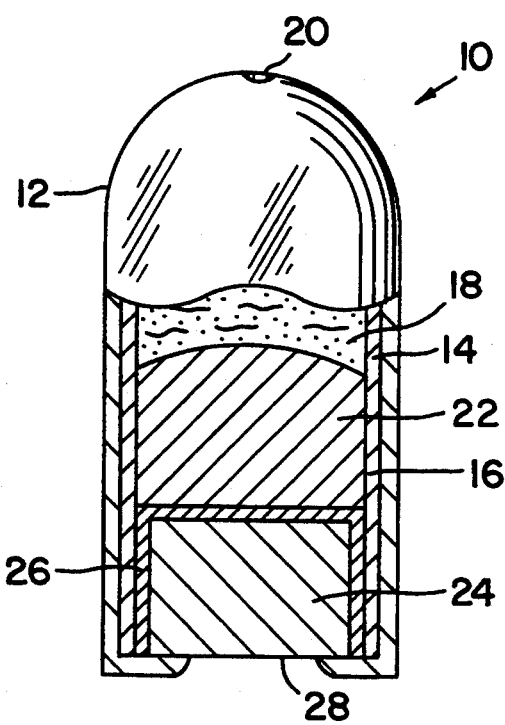
FIG. 1 is a partial cross-sectional view of one embodiment of an improved ruminal delivery device and barrier means according to the present invention.

FIG. 1 illustrates a ruminal device 10 having a semipermeable wall 12 which surrounds an optional internal capsule wall 14 and defines an internal compartment 16, which is partially shown in FIG. 1. The agent or drug to be delivered can be dispersed throughout a drug composition 18, which is delivered through an exit orifice 20 by pressure exerted upon said composition by an osmotically activated expandable member 22. A density element 24 is situated at the end of the device 10 opposite from the exit orifice 20. Present between density element 24 and expandable member 22 is a gas-impermeable barrier means 26 for keeping gas evolved as a result of corrosion of the density element from entering into the expandable member 22 and the drug formulation 18. That portion of density element 24 facing to the lower or bottom end 28 of device 10 is not enclosed by wall 12 or barrier means 26, in part so that the evolved gases can vent to the exterior environment.

Figure 2:
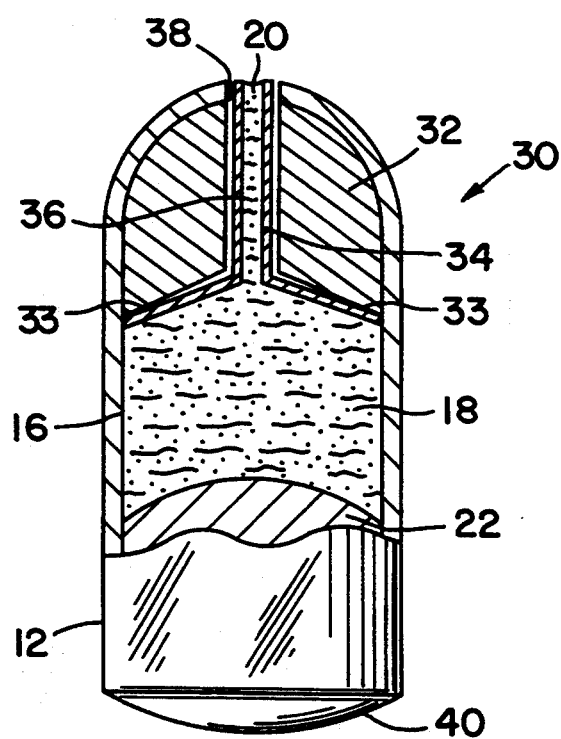
FIG. 2 is a partial cross-sectional view of another embodiment of an improved ruminal delivery device and barrier means according to the present invention.

FIG. 2 illustrates another embodiment of a ruminal delivery device 30, which has a semipermeable wall 12, an internal compartment 16 (partially shown), exit orifice 20, drug formulation 18, expandable member 22, density element 32, and impermeable barrier means 34. For purposes of illustration only, device 30 differs from device 10 by having only a single wall 12 and having a rounded bottom 40. In device 30, the density element 32 is positioned near the exit orifice 20 and includes a bore or passageway 36 extending through the density element to provide contact between drug formulation 18 and the exterior through exit orifice 20. Barrier means 34, also having a bore therethrough, is placed in the passageway 36 and otherwise between the density element and the drug formulation throughout the interface between the two so that there is no contact between them, to provide a barrier for keeping evolved gases from passing into and displacing the drug formulation.

Figure 6:
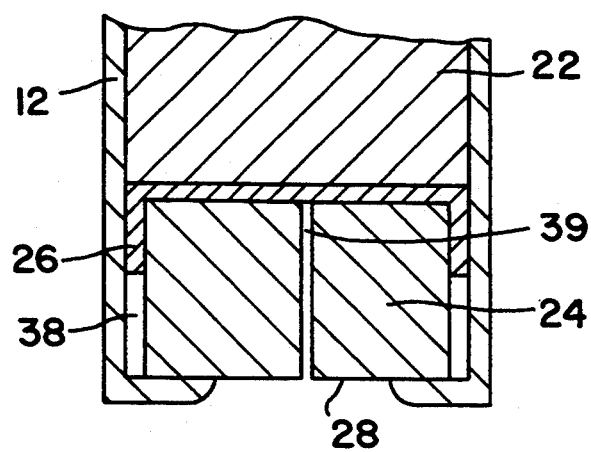
FIG. 6 is an enlarged cross-sectional view of a portion of an improved delivery device showing yet another embodiment of a barrier means.

In a presently preferred embodiment, there is a space or vent 38 between the density element 32 and the barrier means 34 for providing a channel for the evolved gas to vent to the outside of the device. This vent 38 may be provided in any of a number of ways known to the art such as, for example, having the barrier means 34 being in contact with the density element 32 in only a portion of the interface between them, as illustrated in device 30 at point 33. This is also illustrated in FIG. 6, where the barrier means 26 is in contact with only a portion of the density element 24 to provide vent 38. Vent 38 may alternatively be provided by, for example, one or more protrusions extending from either the density element or the barrier means, or both, to separate apart the density element and the barrier; or by one or more grooves present on the interface surface of either the density element or the barrier means, or both. The number of protrusions or grooves is not critical and may be from 1 to 300 or more. In a further alternative embodiment, vents, bores or channels are formed within the density element (by drilling, molding or other means known in the art) and extending through the density element to the exterior environment. This is illustrated in FIG. 6 where bore or vent 39 extends through density element 24 to allow evolved gases to escape to the environment at bottom end 28. Bore or vent 39 may extend completely through the density element, as shown, or it may extend only partially through the density element. The number of vents or bores is not critical and may be from 1 to 50 or more. Other ways of providing a venting means are known or can be determined without undue experimentation by those skilled in the art.

Figure 3:
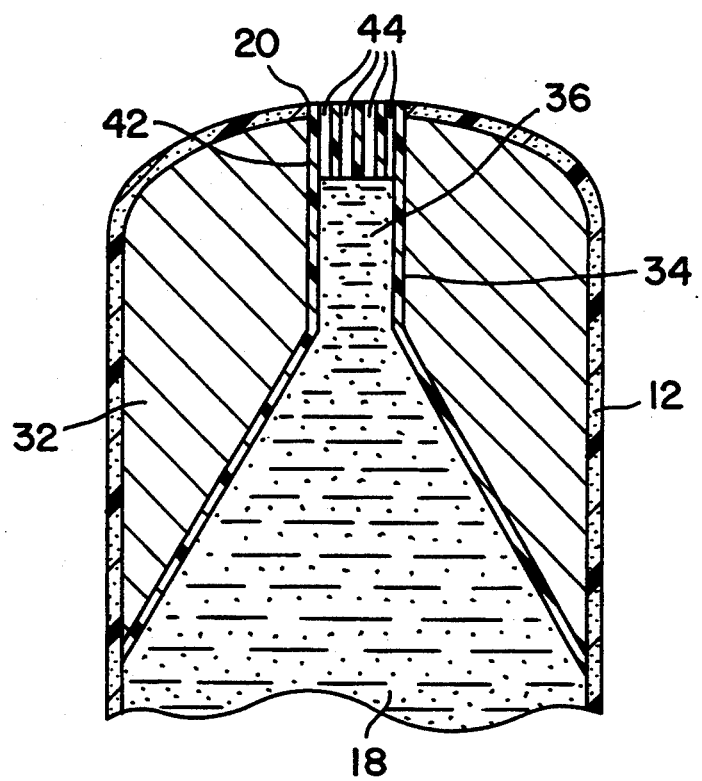
FIG. 3 is an enlarged cross-sectional view of a portion of an improved delivery device showing yet another embodiment of a barrier means, including an exit port screen, according to the present invention.

In certain uses of a ruminal delivery device, it is desireable to have a screen across the exit orifice for keeping external matter out of the device or for providing a back-pressure for improved drug delivery from the device. Capscreens are disclosed in U.S. Pat. Nos. 4,872,873, 5,122,128 and 5,213,809, the disclosures of which are incorporated herein by reference. In one contemplated embodiment of the present invention, shown in FIG. 3, an exit port screen 42 is incorporated into the barrier means 34 of the present invention. Exit port screen 42 is located at that end of barrier means 34 which is adjacent to the exit orifice 20 of the device and integral with the exit orifice. Exit port screen 42 may, optionally, extend within at least a portion of bore or passageway 36 (shown). Exit port screen 42 covers the exit orifice and has a plurality of screen passageways 44 extending through it for allowing passage of the drug formulation 18 to the external environment. The number of screen passageways 44 is not critical and will depend on the use contemplated for the exit port screen 42, the drug formulation to be delivered, and other considerations pertinent to the particular contemplated use, as is taught in the above cited patents, previously incorporated by reference.

Figure 4:
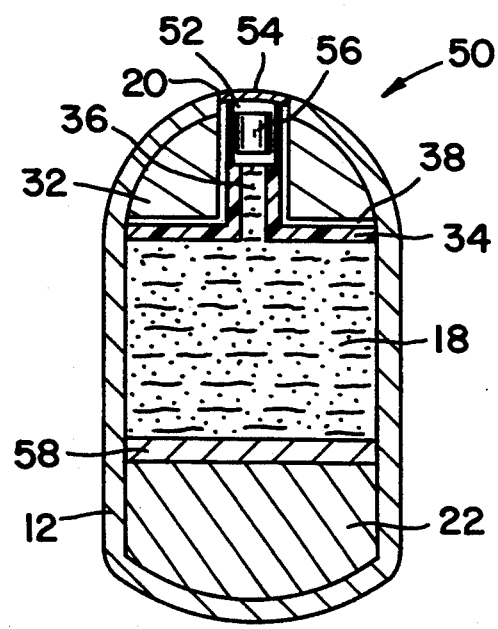
FIG. 4 is a cross-sectional view of a different embodiment of an improved delivery device and a barrier means, including means for maintaining a loading dose tablet, according to the present invention.

In other contemplated uses of a ruminal delivery device, it may be desireable to include a loading dose for providing immediate delivery of a drug during the period of startup of the device itself. See, U.S. Pat. No. 5,045,082, the disclosure of which is incorporated herein by reference. In one embodiment of the present invention, device 50 as shown in FIG. 4, a loading dose chamber 52 is incorporated into the barrier means 34 adjacent to and integral with the exit orifice 20 and the bore or passageway Loading dose chamber 52, together with retaining means 54, is designed to retain a loading dose 56 which contains a formulation for release of drug or other therapeutic agent. The retaining means 54 which covers the loading dose chamber 52 functions to keep the loading dose 56 as an integral part of the dispensing device 50 while allowing consistent dispersion of the loading dose to the external environment over time, as is taught in the above cited patent, previously incorporated by reference. Evolved gases which enter vent 38 are also released through the retaining means, which extends from the loading dose chamber to cover the vent 38 where it opens to the external environment.

In a presently preferred embodiment of the delivery device herein, a moveable partition layer 58 is present between the drug formulation 18 and the expandable member 22 to maintain the separate identity of the two components and to assist in the expulsion of the drug formulation from the device into the external environment. Partition layers are well known in the art and are further described in, for example, U.S. Pat. Nos. 4,772,474 and 4,844,984, the disclosures of which are incorporated herein by reference.

The barrier means of this invention are characterized by being essentially impermeable to any gases, and in particular to hydrogen gas, which are evolved as part of the corrosion process of metallic density elements. By "essentially impermeable" is meant that the barrier material is not permeable to such gases at all, or that the gases permeate the material in only a negligible amount, of no greater than about $20 \times 10^{-10}$ cm/sec-cmHg. The materials suitable for the barrier means are any materials that are essentially impermeable to gases and that are additionally inert to the drug formulation, the density element and the other components of the delivery device. Such characteristics are known in the art or can be determined without undue experimentation. Materials may be selected from, but are not limited to, polyvinyl alcohol; polypropylene; cellulose; cellulose esters; Delrin ®; fluorocarbon polymers; polyamides; polyesters; polyolefins; noncorrosive metals such as stainless steel; nylon; and the like.

The barrier means can be manufactured according to processes well known in the polymer and plastic arts, such as by injection molding, compression molding, casting, mechanical machining, and the like. Where venting means are not present between the density element and the barrier means, the barrier means may be a coating applied directly onto the surface of the density element by coating processes as are known in the art. When the barrier means is an insert, it is sized and shaped to be placed between the density element and the other components within a ruminal drug delivery device.

Figure 5:
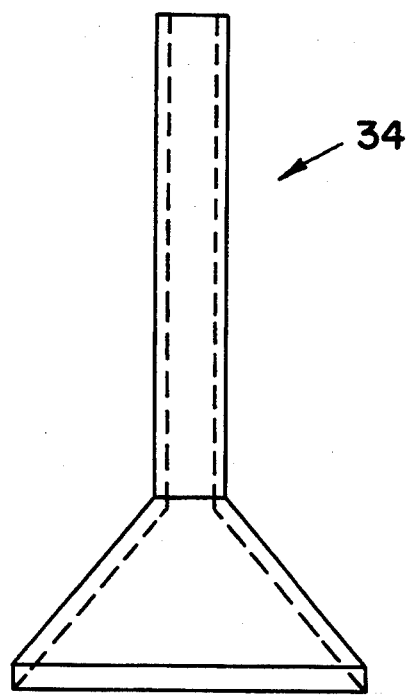
FIG. 5 is a side view of one embodiment of the gas-impermeable barrier means of the present invention.

A representative embodiment of an insert barrier article of the present invention is shown in FIG. 5. FIG. 5 illustrates an insert 34 (which is shown in FIG. 2 in cross-section positioned in a ruminal delivery device). Barrier insert 34 is funnel-shaped, having a circular cross-section along its longitudinal axis. It has the dimensions indicated in FIG. 5 and is sized and shaped to fit within a density element (32 in FIG. 2) with a clearance of about 7 mil (0.18 mm) to form a channel for escaping gases (vent 38 in FIG. 2). In a presently preferred embodiment, the barrier insert of the present invention is manufactured of Delrin ® ((polyoxymethylene) acetyl resin homopolymer; DuPont).

The term "drug" is used broadly and generically herein to refer to any drug or other beneficial agent which it is desired to deliver to a ruminant animal from a ruminal delivery device, and the present invention is not limited to any particular drugs. Such beneficial agents are known to the art and representative agents are disclosed in the patents incorporated herein by reference.

The following examples are illustrative of the present invention. They are not to be construed as limitations of the scope of the invention. Variations and equivalents of these examples will be apparent to one skilled in the art in light of the present disclosure, the drawings, and the claims herein. All percentages are weight-weight percent, and all temperatures are in degrees Celsius, unless otherwise noted.

EXAMPLE 1

An improved ruminal delivery device according to the present invention is prepared as follows.

A semipermeable wall was prepared by sizing and then mixing together 50.5 g cellulose acetate butyrate having a butyryl content of 17% and an acetyl content of 29% (Eastman), 17.5 g cellulose acetate having an acetyl content of 39.8% (Eastman), 22.0 g triethyl citrate (Citroflex-4 ®, Morflex, Inc.), 6.0 g tributyl citrate (Citroflex-2 ®, Pfizer, Inc.), and 4.0 g polyethylene glycol having a molecular weight of 400 (PEG 400, Union Carbide). After mixing for 20 minutes, the material was transferred to the feed hopper of an injector molder equipped with a suitable mold to produce a cellulosic membrane cup weighting 10.1 g and having the following dimensions: 7.9 cm height, 2.5 cm width, and wall thickness of 0.17 cm.

An osmotic expandable member was prepared by blending together 60.3 g sodium salt of polyacrylic acid having a MW of 3,000,000 (Sodium Carbomer ®934P, B. F. Goodrich Chemical), 0.9 g polyvinylpyrrolidone (PVP), 0.9 g magnesium stearate, 12.9 g water, and 25 g sodium chloride. 8.41 Grams of the blend was compressed under 10 tons of force to form tablets which conform to the internal diameter of the membrane cups prepared above. One of the compressed osmotic tablets was inserted into the membrane cup.

A placebo "drug" formulation was prepared by melting a microcrystalline wax (Multiwax ® X145A; Witco Chemical Co.) and, with the temperature maintained at 68° C., delivering 11.5 g (about 12.8 mL) of the wax to the membrane cup assembly over the osmotic tablet.

A sintered iron density element was prepared, having a 5.1 mm diameter bore therethrough and shaped generally as illustrated in FIG. 2 and of a size for placement in the membrane cup.

A barrier insert as illustrated in FIG. 5 was prepared by machining a funnel-shaped insert from Delrin ® in the shape and dimensions set out in FIG. 5 to fit into the inside of the density element with about 7 mil (0.18 mm) clearance between the insert and most of the density element.

The barrier insert was placed into the density element so that it is situated next to or against the interior portion of the element, after which the density element was inserted into the open end of the membrane cup assembly and seated against the "drug" formulation. The barrier insert separates the drug formulation from exposure to the density element. The protruding lip of the cup was heated until softened using a hot air gun, and the lip was crimped over the density element, leaving the exit orifice open.

EXAMPLE 2

A ruminal delivery device identical to the device in Example 1 was prepared, except that a barrier insert was not placed into the density element, resulting in a prior art ruminal bolus having an untreated density element placed in contact with drug formulation.

In the same manner, a prior art delivery device was prepared having an impregnated density element and no barrier insert. The density element was impregnated during manufacture with microcrystalline wax Multiwax 180M, following the procedures of U.S. Pat. No. 5,206,024.

EXAMPLE 3

The delivery device of the present invention of Example 1 was compared, in vitro, with the prior art devices of Example 2 to compare delivery profiles and presence or absence of gas within the drug formulation, as follows.

Figure 7:
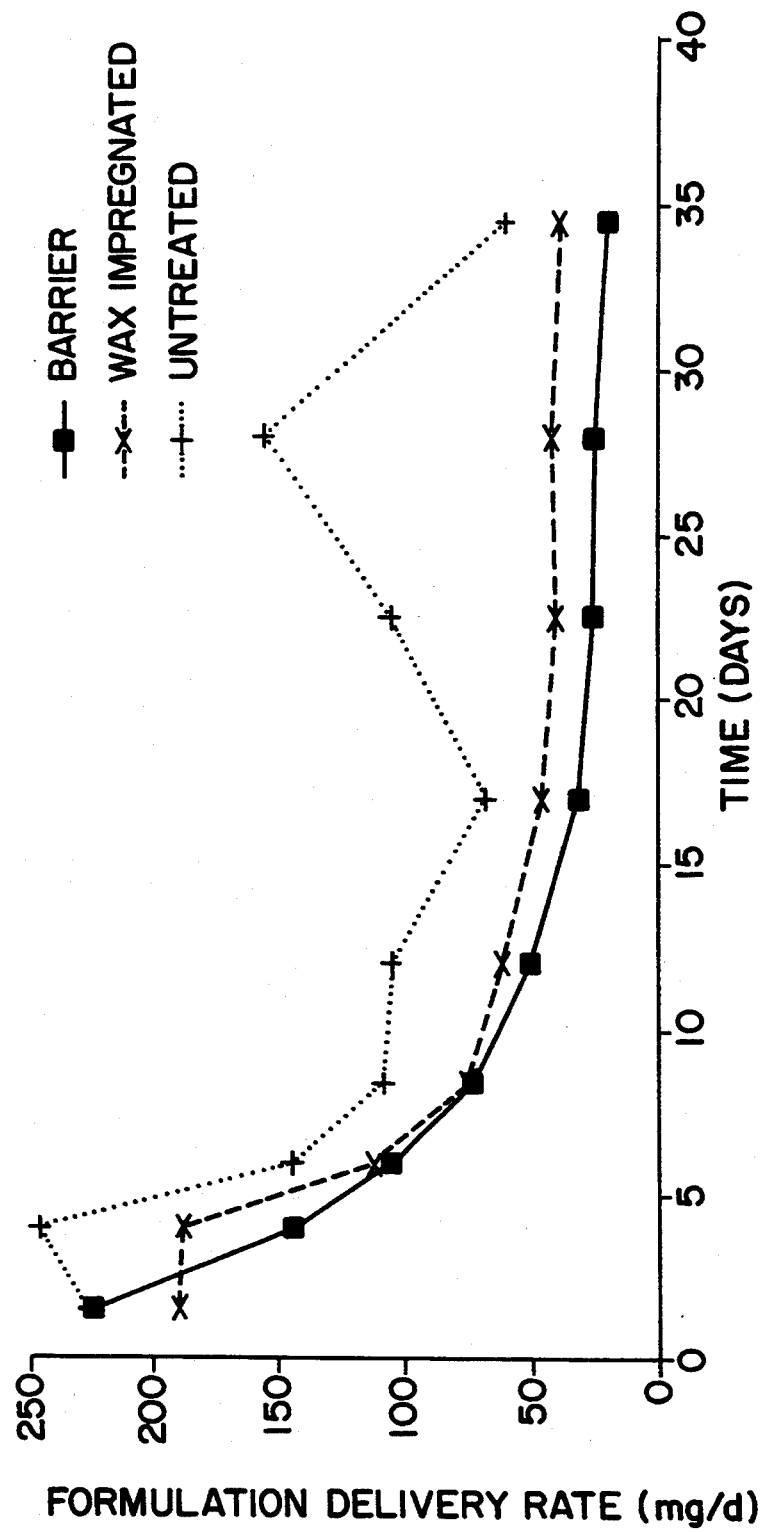
FIG. 7 is a graph illustrating the release rate of devices of the present invention in comparison with release rates of prior art devices.

The devices (n=8) were placed in deionized water and maintained at ruminant body temperature. Material which extruded from the devices was removed periodically and weighed to determine the release rate from each of the devices. The comparative averaged release rates for the devices are presented in FIG. 7.

At the end of the testing, each of the devices was cut open to determine the presence or absence of voids caused by gas bubbles. Out of the eight devices in each set, there were severe voids (15-25 mm) in three of the untreated devices, there were minor voids (2-5 mm) in three of the wax-impregnated devices, and there were no voids whatever in any of the devices of the invention having barrier inserts.

EXAMPLE 4

A delivery device for the delivery of ivermectin is prepared as described in Example 1, except as follows.

After the osmotic expandable tablet is inserted into the membrane cup, two grades of microcrystalline wax (49 g Multiwax ® 180M and 49 g Multiwax ® X145A) and 2 g Cab-0-Sil ® (colloidal silicone dioxide, Cabot Corp.) are mixed together, and the mixture is heated to 85° in a hot-melt tank pump. 3.0 Grams (about 3.3 mL) of the wax mixture is poured into the membrane cup in laminated arrangement above the osmotic expandable tablet to form a partition layer.

An ivermectin drug formulation is prepared as follows. 831 g Multiwax X145A and 20 g Cab-0-Sil are melted, after which the temperature is adjusted to 80° C. Ivermectin (149 g) is added, using a high sheer mixing apparatus. The temperature of the formulation is maintained at 68° C. while 8.5 g (about 9.5 mL) of the formulation is delivered to the membrane cup assembly over the partition layer.

The barrier insert and the density member are then added as in Example b 1 to give an ivermectin ruminal bolus.

What is claimed is:

1. An improved ruminal drug delivery device comprising a semipermeable membrane having an exit orifice and defining a compartment, the compartment containing an osmotic expandable member, a drug formulation containing a drug to be dispensed, and a density element, wherein the improvement comprises a barrier means between the density element and other components within the compartment for separating the density element from the other components, the barrier means being essentially impermeable to gases.

2. An improved ruminal delivery device according to claim 1 wherein the barrier means is an insert.

3. An improved ruminal delivery device according to claim 1 wherein the barrier means is a coating on the density element.

4. An improved ruminal delivery device according to claim 1 wherein the barrier means is selected from the group consisting of polyvinyl alcohol, polypropylene, cellulose, cellulose esters, (polyoxymethylene) acetyl resins, fluorocarbon polymers, polyamides, polyesters, polyolefins, nylon, and noncorrosive metals.

5. An improved ruminal delivery device according to claim 1 wherein the drug is ivermectin.

6. An improved ruminal delivery device according to claim 1 wherein the improvement further comprises venting means between the density element and the barrier means.

7. An improved ruminal delivery device according to claim 1 which further comprises a moveable partition layer between the drug formulation and the expandable member.

8. An improved ruminal delivery device according to claim 1 wherein the barrier means is an insert and the insert further comprises an exit port screen.

9. An improved ruminal delivery device according to claim 1 wherein the barrier means is an insert and the insert further comprises a loading dose chamber and a loading dose.

10. A method for providing a consistent delivery of drug from a ruminal delivery device, the method comprising:

a) placing into the rumen of a ruminant animal an improved ruminal delivery device, the delivery device comprising a semipermeable membrane defining a compartment, the compartment containing an osmotic expandable member, a drug formulation containing a drug to be dispensed, a density element, and an exit orifice, wherein the improvement comprises a barrier means separating the density element from the other components within the delivery device, the barrier means being essentially impermeable to gases; and b) allowing fluid from the ruminal environment to be taken up by the osmotic expandable member for delivering the drug from the device.

11. A method according to claim 10 wherein the barrier means is an insert.

12. A method according to claim 10 wherein the barrier means is a coating on the density element.

13. A method according to claim 10 wherein the barrier means is selected from the group consisting of polyvinyl alcohol, polypropylene, cellulose, cellulose esters, (polyoxymethylene) acetyl resins, fluorocarbon polymers, polyamides, polyesters, polyolefins, nylon, and noncorrosive metals.

14. A method according to claim 10 wherein the drug is ivermectin.

15. A method according to claim 10 wherein the improvement to the ruminal delivery device further comprises venting means between the density element and the barrier means.

16. A method according to claim 10 wherein the ruminal delivery device further comprises a partition layer between the drug formulation and the expandable member.

17. A method according to claim 10 wherein the barrier means is an insert and the insert further comprises an exit port screen.

18. A method according to claim 10 wherein the barrier means is an insert and the insert further comprises a loading dose chamber and a loading dose.

19. An insert for use in a ruminal drug delivery device, the insert being essentially gas-impermeable and being sized and shaped to be placed between a density element and other components within the ruminal delivery device.

20. An insert according to claim 19 which comprises a material selected from the group consisting of polyvinyl alcohol, polypropylene, cellulose, cellulose esters, (polyoxymethylene) acetyl resins, fluorocarbon polymers, polyamides, polyesters, polyolefins, nylon, and noncorrosive metals.

21. An insert according to claim 19 which further comprises venting means.

22. An insert according to claim 21 wherein the venting means is selected from the group consisting of one or more protrusions, one or more grooves, one or more bores, and combinations thereof.

23. An insert according to claim 19 which further comprises an exit port screen.

24. An insert according to claim 19 which further comprises a loading dose chamber and a loading dose.

* * * * *